United States Patent
Schneider et al.

(10) Patent No.: US 6,964,733 B1
(45) Date of Patent: Nov. 15, 2005

(54) PLANAR SENSOR ELEMENT

(75) Inventors: Gerhard Schneider, Pettstadt (DE); Harald Neumann, Vaihingen (DE)

(73) Assignee: Robert Bosch GmbH, Stuttgart (DE)

( * ) Notice: Subject to any disclaimer, the term of this patent is extended or adjusted under 35 U.S.C. 154(b) by 0 days.

(21) Appl. No.: 09/176,124

(22) Filed: Oct. 21, 1998

(30) Foreign Application Priority Data

Oct. 22, 1997 (DE) ................. 197 46 516

(51) Int. Cl.[7] .............. G01N 27/409; G01N 27/41
(52) U.S. Cl. ................. 204/426; 204/427
(58) Field of Search .................. 204/421–429

(56) References Cited

U.S. PATENT DOCUMENTS

| | | | | |
|---|---|---|---|---|
| 4,505,806 A | * | 3/1985 | Yamada | 204/427 |
| 4,505,807 A | * | 3/1985 | Yamada | 204/427 |
| 4,647,364 A | * | 3/1987 | Mase et al. | 204/426 |
| 4,718,999 A | * | 1/1988 | Suzuki et al. | 204/406 |
| 4,755,274 A | * | 7/1988 | Mase et al. | 204/426 |
| 4,769,123 A | * | 9/1988 | Mase et al. | 204/425 |
| 5,529,677 A | | 6/1996 | Schneider et al. | |
| 5,879,525 A | * | 3/1999 | Kato | 204/424 |

FOREIGN PATENT DOCUMENTS

DE     42 31 966     3/1994

* cited by examiner

*Primary Examiner*—Kaj K. Olsen
(74) *Attorney, Agent, or Firm*—Kenyon & Kenyon

(57) ABSTRACT

A planar sensor element for determining gas components, which includes a layer structure with a heating element integrated therein with a layer-shaped heating conductor. The heating conductor is arranged in a layer plane of the layer structure so that an at least approximately homogeneous distribution of the heating power of the heating element over the cross-section of the layer structure is obtained.

13 Claims, 1 Drawing Sheet

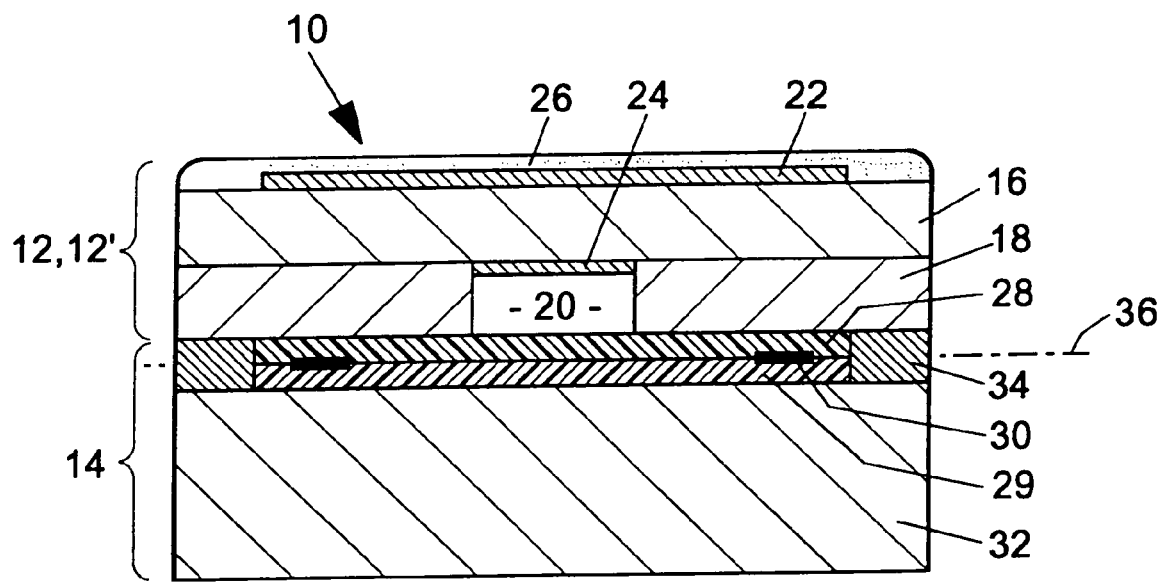
Figure

PLANAR SENSOR ELEMENT

FIELD OF THE INVENTION

The present invention relates to a planar sensor element for determining gas components, in particular for determining the oxygen level in internal combustion engine exhaust gases.

BACKGROUND INFORMATION

A conventional sensor element is described in, for example, German Patent Application No. 42 31 966 (corresponding to U.S. Pat. No. 5,529,677), which is made of a composite of individual foils arranged in consecutively superimposed layers. Function layers such as electrodes, printed conductors and an electric resistance heating element are arranged between the individual foils. The function layers and the heating element are printed onto the unsintered (green) foils using screen printing, for example. Then, the foils are placed one on top of the other, laminated and subsequently sintered. In the planar sensor element of this type, the resistance heating element is arranged in one of the layers between an external cover foil and an adjacent layer structure. The resistance heating element is embedded between two electrically insulating layers (e.g., $Al_2O_3$), so that the heating conductor is electrically insulated from the adjacent foils. On its side opposite a side of the cover foil, the layer structure has a considerably greater thickness than the cover foil adjacent to the other side. Due to this highly asymmetrical arrangement of the heating element with respect to the layer sequence of the layer structure, the cover foil heats up much more than the layer structure provided with function layers. The non-homogeneous distribution of the heating power results in increased heat shock sensitivity of the planar sensor element when the temperature varies.

SUMMARY OF THE INVENTION

The planar sensor element according to the present invention is advantageous in that the heating power is homogeneously distributed over the cross-section of the sensor element.

Thus, a resistance of the sensor element to temperature variations and thermal shock is improved. Furthermore, the efficiency of the heating element is enhanced.

It is also advantageous if a covering layer structure is made of a single foil having a thickness, in the unsintered (green) state, of 0.6 to 1 mm, preferably 0.8 mm. The layer structure adjacent to the resistance heating element on the opposite side and containing the function layers (function layer-side layer structure) has a total thickness approximately equal to that of the cover foil or the cover foil-side layer structure, according to the number of foils and other layers, such as a cover layer on the external electrode. This means that the thickness of the function layer-side foils $d_F$ for uniform thickness distribution is defined by $$d_F = (d_{F1} - d_D)/n,$$

where $d_{F1}$ is the thickness of the unsintered cover foil, $d_D$ is the thickness of the cover layer or protective layer arranged on the external electrode, and n is the number of function layer-side foils. In this calculation, it is assumed that the insulation layers have at least approximately the same thickness on both sides of the heating element.

BRIEF DESCRIPTION OF THE DRAWING

The FIGURE shows an exemplary embodiment of a sensor element according to the present invention.

DETAILED DESCRIPTION

The FIGURE shows a cross section through an exemplary embodiment of a planar sensor element 10, which may be used, e.g., for determining the oxygen level in exhaust gases of internal combustion engines or combustion systems. The sensor element shown in this embodiment is a lambda-1 sensor (e.g., a Nernst sensor). The design and function of such a sensor are generally known.

Sensor element 10 has, when unsintered, an elongated, plate-shaped design, which contains a plurality of layers arranged one on top of the other in a layer structure. The layers, when unsintered (green), are basically formed by oxygen ion-conducting solid electrolyte foils.

In this embodiment according to the present invention, sensor element 10 has an electrochemical measuring cell 12 and a heating element 14. Measuring cell 12 has a function layer-side layer structure 12' with a first foil 16 and a second foil 18. A reference channel 20 is integrated in second foil 18. A measuring electrode 22 is arranged on the measuring-gas side surface of foil 16, and a reference electrode 24 is arranged on the surface associated with reference channel 20. A porous cover layer 26 having a thickness of approximately 0.1 mm is placed on measuring electrode 22.

Heating element 14 has a heating conductor 30, embedded in two insulating (insulation) layers 28 and 29, the two insulation layers 28, 29 having essentially the same thickness. An external covering foil 32 follows first insulation layer 29. In order to seal porous insulation layers 28, 29 in a gas-tight manner, a sealing frame 34 is positioned around them, which is manufactured, for example, by printing solid electrolyte material on foils 18, 32, arranged on both sides of insulation layers 28, 29.

Heating conductor 30 is in a layer plane 36, centered with respect to the layer structure above or below. Due to this fact, the layer thickness of foils 16, 18 of measuring cell 12 is to be dimensioned according to the thickness of cover foil 32, taking into account the thickness of cover layer 26, or vice-versa. In this embodiment, the unsintered cover foil has a thickness of 0.8±0.1 mm. The thickness of porous cover 26 layer is assumed to be approximately 0.1 mm. This results in a layer thickness for first and second foils 16, 18 of approximately 0.35±0.05 mm each. The thickness ratio of foils 16, 18, 32 remains basically preserved even after sintering as a layer thickness ratio, based on a sintering shrinkage of approximately 20%.

It is also possible for the two foils 16, 18 to have different thicknesses. It is essential, however, that the total thickness of the function layer-side layer structure of the sensor element, considering other layers such as cover layer 26, for example, be (at least approximately) equal to the thickness of cover foil 32 or a cover foil-side layer structure used instead of cover foil 32.

Foils 16, 18, 32 are made of stabilized zirconium oxide, for example. In order to achieve densely sintered bonding, sealing frame 34 is made of the same material as the adjacent foils 18 and 32. Electrodes 22, 24 and heating conductor 30 are made of a platinum cermet, for example. Insulation layers 28, 29 are made of $Al_2O_3$ in this embodiment, an insulation layer 29 being initially printed onto cover foil 32.

Heating element 30 is also applied to insulation layer 29 by printing. Finally, one-half of sealing frame 34, for example, is also applied around insulation layer 29 by printing.

To manufacture the layer structure of measuring cell 12, the two electrodes 22, 24, with the leads not illustrated in detail, are printed onto foil 16. The additional insulation layer 28 and the second half of sealing frame 34 are applied onto second foil 18.

The function layer-side and heating element-side layer structures thus formed are laminated with the unsintered foils using binder layers applied between the foils, and are sintered at a temperature of 1400° C., for example. After sintering, the plate-shaped sensor element with a rectangular cross section is obtained.

The layer structure described is, however, not limited to the exemplary embodiment with a Nernst type sensor element 10. The present invention can also be used with a sensor element having more than three foils. Such a sensor is, for example, a broadband sensor in which a pump cell and a concentration cell (Nernst cell) are provided instead of measuring cell 12.

What is claimed is:

1. A planar sensor element for determining at least one gas component, comprising:
   a layer structure including:
     a measuring cell layer;
     a covering layer; and
     a heating element disposed directly between the measuring cell layer and the covering layer and generating a heating power, a layer-shaped heating conductor being embedded in the heating element in a layer plane of the layer structure;
   wherein the layer plane is at least approximately vertically centered with respect to the sensor element, the measuring cell layer, covering layer and layer plane extending in a horizontal direction;
   wherein the covering layer adjoins the heating element on a side of the heating element facing away from the measuring cell layer and does not form part of an oxygen pump cell or an oxygen concentration cell; and
   wherein the covering layer extends from the side of the heating element facing away from the measuring cell layer to an end face of the planar sensor element.

2. The planar sensor element according to claim 1, wherein the planar sensor element is formed using a sintering process,
   wherein, before the layer structure is sintered, the measuring cell layer includes at least two measuring cell layer foils and the covering layer includes at least one covering layer foil, the covering layer foil having a predetermined thickness, and
   wherein a total thickness of the at least two measuring cell layer foils is at least approximately equal to the predetermined thickness.

3. The planar sensor element according to claim 2, wherein the layer structure includes a further layer having a further thickness, and wherein the total thickness includes the further thickness.

4. The planar sensor element according to claim 1, wherein the layer structure further includes a plurality of electrically insulating layers, a first thickness of one of the electrically insulating layers being approximately equal to a second thickness of another one of the electrically insulating layers, and wherein the heating conductor is embedded in the electrically insulating layers, the electrically insulating layers being formed on both sides of the heating conductor.

5. The planar sensor element according to claim 4, wherein the layer structure further includes a sealing frame surrounding the electrically insulating layers, the sealing frame having a frame thickness which is equal to a thickness of the electrically insulating layers.

6. The planar sensor element according to claim 5, wherein the electrically insulating layers include two electrically insulating layers.

7. The planar sensor element according to claim 1, wherein the layer-shaped heating conductor is arranged in the layer plane of the layer structure to obtain an at least approximately homogeneous distribution of the heating power over a cross-section of the sensor element perpendicular to the layer structure.

8. The planar sensor element according to claim 1, wherein the cover layer comprises an entirety of the planar sensor element on one side of the heating element.

9. The planar sensor element according to claim 1, wherein the covering layer is made from stabilized zirconium oxide.

10. The planar sensor element according to claim 1, wherein the measuring cell layer contacts a first planar surface of the heating element and the covering layer contacts a second opposing planar surface of the heating element.

11. The planar sensor element according to claim 1, further comprising a sealing frame around the heating element configured to seal the heating element in a gas-tight manner.

12. A planar sensor element for determining at least one gas component, comprising:
   a layer structure including:
     at least one of an oxygen pump layer and an oxygen concentration layer;
     a covering layer; and
     a heating element generating a heating power disposed directly between the covering layer and the at least one of a oxygen pump layer and oxygen concentration layer, a layer-shaped heating conductor being embedded in the heating element in a layer plane of the layer structure;
   wherein the layer plane is at least approximately vertically centered with respect to the sensor element, the (i) at least one of an oxygen pump layer and an oxygen concentration layer, (ii) covering layer and (iii) layer plane extending in the horizontal direction;
   wherein the covering layer adjoins the heating element on a side of the heating element facing away from the measuring cell layer and does not form a part of another oxygen pump cell or another oxygen concentration cell; and
   wherein the covering layer extends from the side of the heating element facing away from the measuring cell layer to an end face of the planar sensor element.

13. A planar sensor element for determining at least one gas component, comprising:
   a layer structure including:
     a measuring cell layer having at least one surface;
     a covering layer; and
     a heating element disposed directly between the measuring cell layer and the covering layer and generating a heating power, a layer-shaped heating conductor being embedded in the heating element in a layer plane of the layer structure; and
     at least one electrode, each electrode arranged on a respective surface of the measuring cell layer;

wherein the layer-shaped heating conductor is arranged in a layer plane of the layer structure to obtain an at least approximately homogeneous distribution of the heating power over a cross-section of the sensor element perpendicular to the layer structure;

wherein the layer plane is at least approximately vertically centered with respect to the sensor element, the measuring cell layer, covering layer and layer plane extending in the horizontal direction;

wherein the covering layer adjoins the heating element on a side of the heating element facing away from the measuring cell layer and does not form part of an oxygen pump cell or an oxygen concentration cell; and wherein the covering layer extends from the side of the heating element facing away from the measuring cell layer to an end face of the planar sensor element.

* * * * *